(12) United States Patent
Lakshman et al.

(10) Patent No.: US 8,871,280 B1
(45) Date of Patent: Oct. 28, 2014

(54) COMPOSITIONS AND METHODS FOR TREATING FUNGAL ACTIVITY IN PLANTS OR SOIL

(75) Inventors: Dilip K. Lakshman, Greenbelt, MD (US); Kamlesh R. Chauhan, Laurel, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 339 days.

(21) Appl. No.: 13/230,152

(22) Filed: Sep. 12, 2011

(51) Int. Cl.
*A61K 36/47* (2006.01)
*A61K 36/534* (2006.01)
*A61K 36/00* (2006.01)

(52) U.S. Cl.
USPC ............ 424/731; 424/747; 424/773; 424/776

(58) Field of Classification Search
None
See application file for complete search history.

(56) References Cited

U.S. PATENT DOCUMENTS

| | | | | | |
|---|---|---|---|---|---|
| 3,193,451 | A | * | 7/1965 | Reinisch .................. | 514/627 |
| 4,829,085 | A | * | 5/1989 | Wenderoth et al. .......... | 514/522 |
| 2003/0113421 | A1 | | 6/2003 | Wilson et al. | |
| 2008/0131533 | A1 | | 6/2008 | Kvitnitsky et al. | |
| 2009/0017142 | A1 | | 1/2009 | Yang et al. | |

OTHER PUBLICATIONS

Das et al. (1989) JAOCS, vol. 66, No. 7 pp. 938-941.*
Van der Steen et al. (2009) ChemSusChem 2, pp. 692-713.*
Maruzzella et al. (1958) J. Am. Pharm. Assoc. vol. XLVII, No. 4 pp. 250-254.*
Delp (1980) Plant Dis. 64: pp. 652-657.*
Ojiambo et al. (2010) Phytopathology 100(10): pp. 1066-1076.*
Petit et al. (2012) 111: pp. 315-326.*
Yoon et al. (2013) Plant Pathol. J. 29(1): 1-9.*
Novak, A.F., et al.; Antimicrobial Activity of Some Ricinoleic and Oleic Acid Derivatives, JAOCS, 1961, 38: 321-324.
Ahmed, S.M., et al.; Preparation and Characterization of Derivatives of Isoricinoleic Acid and Their Antimicrobial Activity, JAOCS, 1985, vol. 62 (11), 1578-1580.
Varaprasad Bobbarala et al.; Antifungal Activity of Selected Plant Extracts Against Phytopathogenic fungi *Aspergillus niger* F2723; Indian Journal of Science and Technology, 2009, vol. 2 (4), 87-90.
Mutlu, H. et al.; Castor Oil as a Renewable resource for the Chemical Industry, Eur. J. Lipid Sci. Technol., 2010, vol. 112, 10-30.
Plotto, A. et al.; Evaluation of Plant Essential Oils as Natural Postharvest Disease Control of Tomato (*Lycopersicon esculentum*), Issues and Advances in Postharvest Hort. Abstract, 2003, pp. 737-745.
Singh et al.; Control of Stunt Nematode, Phytopathology, 1984, vol. 37, 649.
Lakshman, D.; Arboretum Scientists are Exploring Nature-friendly Ways to Control Soilborne Plant Diseases, Arbor Friends, 2008, 9.

* cited by examiner

*Primary Examiner* — Chris R Tate
*Assistant Examiner* — Russell Fiebig
(74) *Attorney, Agent, or Firm* — John D. Fado; G. Byron Stover

(57) ABSTRACT

Compositions for treating fungal activity in plants, containing castor oil, water, at least one surface active agent, optionally pennyroyal oil, and optionally an agriculturally acceptable carrier. Methods of treating fungal activity in plants, involving administering to the plant or soil an effective fungal treating amount of castor oil, water, at least one surface active agent, optionally pennyroyal oil, and optionally an agriculturally acceptable carrier.

2 Claims, 1 Drawing Sheet
(1 of 1 Drawing Sheet(s) Filed in Color)

COMPOSITIONS AND METHODS FOR TREATING FUNGAL ACTIVITY IN PLANTS OR SOIL

BACKGROUND OF THE INVENTION

The present invention relates to compositions for treating fungal activity in plants or soil, containing castor oil, water, at least one surface active agent, optionally pennyroyal oil, and optionally an agriculturally acceptable carrier. The present invention also relates to methods of treating fungal activity in plants or soil, involving administering to the plant or soil an effective fungal treating amount of castor oil, water, at least one surface active agent, optionally pennyroyal oil, and optionally an agriculturally acceptable carrier.

Approximately, 90% of the 2000 major diseases of principle crops in the US are caused by soilborne plant pathogens, resulting in losses in excess of $4 billion/year and fungi are considered the foremost important plant pathogen (Lewis, J. A., and G. C. Papavizas, Crop Protection, 10: 95-102 (1991); Lumsden, R. D., et al., Formulation and delivery of biocontrol agents for use against soilborne plant pathogens, In: Biorational Pest Control Agents, Hall, F. R., and J. W. Barry, Eds., American Chemical Society, Washington, DC, 1995, pp. 166-182; Agrios, G. N., 2005, Plant Pathology, 5th Edition, Elsevier Academic Press, MA). For example, *Rhizoctonia solani* is a ubiquitous soilborne fungal pathogen causing pre-emergence and seedling damping off, root rot, stunting of plants and aerial blights of economically important crops, forest trees, ornamentals and turfgrasses, as well as decay of postharvest fruits and vegetables (Agrios 2005). Soilborne fungal pathogens have been traditionally controlled using chemical pesticides, some of which deplete non-renewable resources, are inconsistent in efficacies, and are toxic to the environment. As a result, the 1996 "Food and Quality Protection Act" of the United States has dramatically restricted the use of many conventional pesticides upon which the American farmers have long depended. For example, methyl bromide is highly genotoxic and it depletes the ozone; except for critical use exemption, it has been banned for soil fumigation since 2005. Many fungicides, including several alternatives fumigants to methyl bromide (e.g., methyl iodide), are expensive and suspected of introducing new health hazards to agricultural workers (Clifford, B. C., and E. Lester, 1988. Control of Plant Diseases: Costs and Benefits, Blackwell, Oxford, UK; California Dept. of Pesticide Regulation (2010), http://www.cdpr.ca.gov/docs/risk/methyliodide.htm). Also, persistence of many fungicides following their use caused pathogen resistance to several of the fungicides (Delp, C. J., Fungicide resistance in North America, 1988, APS Press, St. Paul, Minn.; Zhao, H., et al., Postharvest Biol. Technol., 56:12-18 (2010)). As a result, eco-friendly management using safer chemicals (i.e., biorationals) are being increasingly sought to control plant diseases.

Thus there exists a need for new compositions and methods to control plant diseases.

SUMMARY OF THE INVENTION

In accordance with the present invention there is provided compositions for treating fungal activity in plants or soil, containing castor oil, water, at least one surface active agent, optionally pennyroyal oil, and optionally an agriculturally acceptable carrier.

Also in accordance with the present invention there is provided methods of treating fungal activity in plants or soil, involving administering to the plant or soil an effective fungal treating amount of castor oil, water, at least one surface active agent, optionally pennyroyal oil, and optionally an agriculturally acceptable carrier.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows soil amendment with 0.3% castor oil (v/w) to suppress cucumber damping off caused by *Rhizocionia solani* as described below. Treatment: (A) Soybean oil only, (B) Soybean oil+*R. solani*, (C) Castor oil only, (D) Castor oil+*R. solani*.

DETAILED DESCRIPTION OF THE INVENTION

The present invention concerns compositions for treating fungal activity in plants or soil, containing castor oil, water, at least one surface active agent, optionally pennyroyal oil, and optionally an agriculturally acceptable carrier. Generally the composition contains about 0.01% to about 5% (e.g., 0.01% to 5%) castor oil, about 0.5% to about 5% (e.g., 0.5% to 5%) lecithin, and about 0.01% to about 1% (e.g., 0.01% to 1%) Tween-20. The present invention also concerns methods of treating fungal activity in plants or soil, involving administering to the plant or soil an effective fungal treating amount of castor oil, water, at least one surface active agent, optionally pennyroyal oil, and optionally an agriculturally acceptable carrier.

The term "treatment" or "treating" as used herein covers any treatment of a fungal disease in a plant or fungal infestation of soil, and includes: (i) preventing the disease from occurring in a plant; (ii) inhibiting the disease, i.e., arresting its development; or (iii) relieving the disease, i.e., causing regression of the disease. References in this specification to treatment or treating include prophylactic treatment as well as the alleviation of symptoms. The amount of the oils or compositions used will be at least an effective amount. The term "effective amount," as used herein, means the minimum amount of the oils or compositions needed to effectively treat the plants or soil when compared to the same plants or soil which are untreated. In general, it is desirable to apply the oils or compositions of the present invention at concentrations in the range of about 0.1% to about 1.0% (e.g., 0.1% to 1.0%) or about 1000 to about 10,000 ppm (e.g., 1000 to 10,000 ppm). However, exact dosages can be determined by one of ordinary skill in the art. With respect to the present invention, preferred dosages are amounts that do not cause necrotic damage to the plant, flowers or fruit. Of course, the precise amount needed will vary in accordance with the particular oil used; the plants to be treated (or the soil to be treated); and the environment in which the plants are located. The precise amount of the oil can easily be determined by one skilled in the art given the teaching of this application. For example, one skilled in the art could follow the procedures utilized below; the oils would be statistically significant in comparison to a negative control. Other compounds may be added to the oils provided they do not substantially interfere with the intended activity and efficacy of the composition; whether or not a compound interferes with activity and/or efficacy can be determined, for example, by the procedures utilized below.

Contemplated for treatment herein are plants having agricultural value such as fruits, vegetables, grains, ornamental stock plants and turf. Berries of commercial interest which are susceptible to fungal decay include, but are not limited to, strawberries, raspberries, blueberries, blackberries, gooseberries, hackberries, boysenberries. Vegetables of intended use include, but are not limited to, beets, beans, cucurbits, eggplants, peppers and tomatoes. Fruit of intended use include, but are not limited to, stone and pome fruits, such asapples, avocados, pears and grapes. The materials are also of use with grains including, but not limited to, rice, oats, maize, wheat and barley. The materials are also useful for growth of stock plants and flowers of various species such as, but not limited to, roses, asters, carnations and chrysanthemums. The oils can be used for soil amendment of potting or field soil, spraying of plant parts, decontamination of irrigation water and soil drenches. In addition, the oils effectively eradicate pathogens through direct contact when used to treat propagating tools, seeds, postharvest grains, fruits and vegetables.

The term "carrier" in the present text, designates an organic or inorganic material, natural or synthetic, with which the oil is combined in order to facilitate its application to the plant, fruit, seeds, or soil. This carrier is therefore generally inert and must be agriculturally acceptable, particularly on the treated plant. The carrier may be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

Surface-active agents (or emulsifiers) are also be utilized. The surface-active agent may be an emulsifying, dispersing or wetting agent of the ionic or nonionic type. The following may be mentioned by way of example: polyacrylic acid salts, lignosulphonic acid salts, phenolsulphonic or naphthalenesulphonic acid salts, polycondensates of ethylene oxide and fatty alcohols or fatty acids or fatty amines, substituted phenols (alkylphenols or arylphenols in particular), ester salts of sulphosuccinic acids, taurine derivatives (alkyltaurates in particular), phosphoric esters of alcohols or of polyoxyethylated phenols. TRITON™ X Series surfactants arc nonionic surfactants which may be utilized. The presence of at least one surface-active agent is essential given that the active material and/or the inert carrier are insoluble in water and that the vector agent of the application is water. Generally 100 ml of selected plant extracts are emulsified in a carrier solution containing, for example, about 0.1 to about 1.0% (w/v) (e.g., 0.1 to 1.0%) L-α-lecithin, about 0.01 to about 0.5% (v/v) (e.g., 0.01 to 0.5%) Triton® X114 (octylphenoxypoly (ethoxyethanol); $C_8H_{16}C_6H_4(—CH_2CH_2O)_{10}H$) and water to obtain a final concentration of 0.1 to 1.0% of PE (0.1 to 1.0 ml of castor oil per 100 gram of soil; 1000-10,000 ppm). Tween®20 (Polysorbate 20; polyoxyethylene (20) sorbitan monolaurate; $C_{58}H_{114}O_{26}$) may also be used.

More generally, the compositions according to the invention may be combined with all those solid or liquid additives found in the usual formulation procedures.

By way of solid composition forms, the following are included: powders for dusting or dispersing (with a content of active material (i.e. fungicide) which may be as high as 95%) and granules, particularly those obtained by extrusion, by compaction, by impregnation of a granulated carrier and by granulation from a powder (the content of active material in these granules being between 1% and 80% in the latter cases).

By way of liquid composition forms or forms intended to constitute liquid compositions on application, the following are included: solutions, in particular water-soluble concentrates, emulsifiable concentrates, emulsions, concentrated suspensions, aerosols, wettable powders (or spray powder) and pastes.

The concentrated suspensions, which can also be applied by spraying, are prepared so as to obtain a stable fluid product which does not form deposits, and they normally contain from 10% to 75% of active material, 0.5% to 15% of surface-active agents, 0.1% to 10% of thixotropic agents, 0% to 10% of appropriate additives, such as pigments, colorants, anti-foams, corrosion inhibitors, stabilizers, penetrating agents and adhesives and, by way of carrier, water or an organic liquid in which the active material is barely soluble or insoluble: some organic solid materials or inorganic salts may be dissolved in the carrier to help prevent sedimentation or as anti-freeze for water.

Castor oil may be employed alone or in the form of mixtures with, for example, pennyroyal oil, and/or a carrier, and/or with other known compatible active agents, especially plant protection agents, such as other fungicides and bactericides, or insectides, acaricides, rodenticides, nematocides, herbicides, fertilizers, growth-regulating agents, etc., if desired, or in the form of a particular dosage preparation for specific application made therefrom, such a solutions, emulsions, suspensions, powders, paste, and granules which are thus ready for use.

The compositions according to the invention may be used in a preventive or curative capacity for combating fungi, particularly of the basidiomycete, ascomycete, oomycete or imperfect fungi types, in particular rusts, oidium, eyespot, fusarioses, *Fusarium roseum, Fusarium nivale*, net blotch, leaf blotch, septoria spot, bunt, rhizoctonioses, and other damping off causing fungi of vegetables and plants in general and, in particular, of cereals such as wheat, barley, rye, oats and their hybrids and also rice and maize.

The compositions according to the invention are active in particular against fungi particularly of the following types: basidiomycetes, ascomycetes, adelomycetes or imperfect fungi such as *Botrytis cinerea, Colletotrichum fragariae, Colletotrichum acutatum, Colletotrichum gloesporiodes, Erysiphe graminis, Puccinia graminis, Puccinia triticina, Puccinia recondita, Uromyces appendiculatus, Phakospora pacchyrhizi, Piricularia oryzae, Cercospora beticola, Puccinia striiformis, Erysiphe cichoracearum, Fusarium oxysporum* (*melonis*, for example), *Pyrenophora avenae, Septoria tritici, Venturia inaequalis, Whetzelinia sclerotiorum, Manilla laxa, Mycosphaerella fijiensis, Marssonina panettoniana, Ahernaria solani, Aspergillus niger, Cercospora arachidicola, Cladosporium herbarum, Helminthosporium oryzae, Penicillium expansum, Pestalozzia* sp., *Phialophora cinerescens, Phoma betae, Phoma foveata, Phoma lingam, Ustilago maydis, Verticillium dahliae, Ascochyta pisi, Guignardia bidwellii, Corticium rolfsii, Phomopsis viticola, Sclerotinia sclerotiorum, Sclerotinia minor, Coryneum cardinale, Rhizoctonia solani.*

The compositions according to the invention are active in particular against soilborne pathogenic fungi, particularly of the following: *Rhizoctonia solani, Pythium* spp., *Botrytis cineria, Thielaviopsis basicola*, and *Fusarium oxysporum.*

They are also active against the following fungi: *Acrostalagmus koningi, Alternaria, Colletotrichum, Diplodia natalensis, Gaeumannomyces graminis, Gibberella fujikuroi, Hormodendron cladosporioides, Lentinus degener or tigrinus, Lenzites quercina, Memnoniella echinata, Myrothecium verrucaria, Paecylomyces varioti, Pellicularia sasakii, Phellinus*

*megaloporus, Polystictus sanguineus, Poria vaporaria, Sclerotium rolfsii, Stachybotris atra, Stereum, Stilbum* sp., *Trametes trabea, Trichoderma pseudokoningi, Trichothecium roseum.*

Unless defined otherwise, all technical and scientific terms used herein have the same meaning as commonly understood by one of ordinary skill in the art to which the invention belongs. The term "about" is defined as plus or minus ten percent; for example, about 100° F. means 90° F. to 110° F. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Fungal isolate and preparation of inoculum: *Rhizoctonia solani* AG-4, isolate Rs 23A is a highly virulent pathogenic isolate which infects many vegetables, ornamentals and turfgrasses (Lewis, J. A., and G. C. Papavizas, Soil Biology and Biochemistry, 9:195-201 (1987)). The fungus was grown in potato dextrose agar (PDA) plates and fungal plugs from the freshly growing mycelium were mixed with moist sterilized cracked wheat in a 2 L flask for 15 days in dark at 22° C. (Lakshman, D. K., et al., Proceedings of the National Academy of Science, USA, 95: 6425-6429 (1998)). The infested wheat was air dried in a sterile hood for 3 days, blended in a homogenizer and sieved through a mesh and stored at 2° C. before soil inoculation. A dose response of the inocula was carried out by thoroughly mixing using 0.25, 0.5, 0.75, 1.0, 1.25 and 1.50 g inoculums per Kg dry weight potting soil plus sterile water to maintain 25-30% moisture and incubating at room temperature for two weeks before sowing cucumber (cv muncher) seeds with the infested soil. The percent germination and post-emergence damping off of cucumber seedlings were recorded. The lowest inoculums dose that induced 100% postemergence damping off was estimated to be 1 to 1.25 g/Kg soil for inocula prepared over the span of the experiments. For soil fumigation with plant extracts (PEs), each time the minimum inoculum dose giving rise to 100% damping off was used.

Plant extracts: All the plant extracts (e.g., oils) or plant derived chemicals used in the experiments (Table 1) are commercially available in the US. We bought those chemicals from various companies. Pennyroyal oil extract was purchased from NOW Foods, Bloomingdale, Ill., and castor oil was purchased from SIGMA-ALDRICH, St. Louis, Mo. (SAFC Supply Solutions, 3050 Spruce Street, St. Louise, Mo.). Castor oil is a vegetable oil from castor beans, extracted similarly to soybean oil or canola oil.

In vitro bioassays: Two in vitro bioassay methods were used to investigate the mycelial growth inhibitory potentials of PEs. In the poison food technique, test chemical/plant extract was mixed at concentrations of 15, 30, 45, 60, 75, and 150 µl per 20 ml autoclaved PDA at 50° C., poured on three sterile disposable plastic plates (100×15 mm, Fisherbrand) at 20 ml/plate and cooled to room temperature to solidify (Dhingra, O.D., and J. B. Sinclair, 1995, Basic Plant Pathology Methods, 2nd Edition, Lewis Publishers, Boca Raton and London). We observed that soybean oil has no effect on the in vitro growth of *R. solani*, thus for negative control only 0.3% soybean oil was suspended in the PDA. Each plate was seeded in the center with a 5 mm diameter agar disk of the freshly grown *Rhizoctonia* pathogen, mycelial side facing the medium, and sealed with stretched Parafilm® M (Fisher Scientific). The plates were incubated in the dark at room temperature and when the pathogen reached to the edge of the plates in the control treatment (soybean oil), radial measurement of fungal growth in plates treated with PEs were recorded by taking three measurements from each plate. The experiment was repeated one more time. The percent mycelial growth inhibition (MGI) due to PE was calculated using the following formula: MGI=(dc−dt)/dt×100 where dc=Avg. radial growth in mm of pathogen in control plate; dt=avg. radial growth in mm of pathogen in treated plate.

In the second protocol, the chemical was kept not in direct contact with the fungus and we hypothesized that the plant extract will most likely influence the growth of the pathogen by fumigation action. In this approach, three sterile 15 mm filter paper (Whatman International Ltd, Maidstone, UK) disks were placed on the edge of each of three plates on the PDA. Each disk was impregnated in the center with various amounts (5-50 ul/disk) of the test solution/suspension. For negative control, only soybean oil was placed in the filter disk. A 5 mm plug of freshly growing pathogen was placed in the middle of the plate, mycelial side facing the medium, and sealed with stretched Parafilm® M. The plates were incubated in inverted position in the dark at room temperature and when the pathogen reached to the edge of the plates in the control treatment (soybean oil), radial measurement of fungal growth facing the disks in plates treated with PEs were recorded by taking three measurements of fungal radial growth facing the disks and three radial fungal growth measurements projecting in between two disks from each plate. The average radial growth was calculated and the experiment was repeated one more time. Percent growth inhibition was calculated as reported for poison bed assay.

The fungicidal and fungistatic potential of the PEs were determined by the method described by Garber and Houstan (Garber R. H., and B. R. Houston, Phytopathology, 49: 449-450 (1959)). In brief, three 5 mm diameter plugs were taken from the peripheral mycelial growth from each plate and placed in a fresh PDA plate. Following incubation at room temperature for 7 days, observations were recorded for new mycelial growth (fungistatic) or no mycelial growth (fungicidal). As control, peripheral mycelial plugs from soybean oil amended PDA plates were checked for fresh mycelial growth in fresh PDA plates.

Soil treatment: For each treatment, 300 g of dry greenhouse *soli* (Pro-mix, Premier Horticulture LTD, Red Hill, Pa.) was thoroughly mixed with *Rhizoctonia* inoculum and incubated for 15 days as described above. The infested soil was subsequently mixed with 100 ml of selected plant extracts emulsified in a carrier solution containing 0.5% (w/v) L-α-lecithin (Sigma Aldrich Corporation), 0.1% (v/v) Triton X114 (Rohm and Haas, Philadelphia, Pa.) and sterile water to obtain a final concentration of 0.3% of PE (0.3 ml of castor oil per 100 gram of soil; 3000 ppm). The infested soil treated with only the carrier solution served as an untreated control. Following the treatment, the soil was thoroughly stirred to mix the contents and incubated in a double polythene bag closed tightly in the dark at room temperature for four days for fumigation to occur. Following the incubation, the bag was opened to allow as much PE to dissipate as possible. This was done by sprinkling the surface soil with sterile water every other day, and stirring the soil once every day for seven days. For assay of effect on seed germination and phytotoxicity of the plant extracts, soil was treated with plant extract formulations alone.

Greenhouse studies: Treated soil from each treatment was distributed to 4-inch plastic pots into which 12 seeds of cucumbers (95-100% germination) were sown and lightly watered to keep soil moist. The treatments were color coded and pots were randomized across treatment. All plants were kept in a greenhouse between 20° C. (night) to 26° C. (day) with 14 h of light. There were three pots per treatment in each experiment, and the experiment was repeated three times. As positive control, a broad spectrum popular soil fungicide Banrot® 40 WP (The Scotts Company, Ohio) was used following manufacturer's recommendation to control the disease. Total number of seedlings without any sign of damping off in each pot was recorded and percentage of disease suppression were calculated four weeks after sowing cucumber seeds.

Results: We utilized both the poison food technique and the filter disk fumigation method to capture both the contact and the fumigative properties of plant extracts on fungal growth inhibition. As presented in Table 1, several plant extracts (e.g., allylanisole, allylisothiocynate, anethole, anise oil, lemon eucalyptus oil) were found to be potent inhibitors of R. solani growth in both the in vitro methods, showing their concordance. In general, if a plant extract was inhibitory to R. solani in the fumigation assay, it was also equally or more effective in the poison bed assay; however, for some other plant extracts, one or the other method showed more inhibition of fungal growth. For example, bay, cinnamon, clove and vetiver oils were more inhibitory by contact actions than by fumigation actions. On the other hand, amyris oil, karanj oil and pink pepper oil surprisingly had no fumigative action even though they showed inhibitory action on R. solani through contact in poison bed assay. A standard fungicide Banrot® 40 WP gave complete inhibition by contact only in the in vitro bioassay.

The fungicidal (total killing) vs. fugistatic (temporary growth inhibition) of the PEs were investigated both by fumigation and contact action in vitro (Table 1). Whereas most of the PEs were fungistatic in nature (e.g., allynaisole, amrys oil, ceder oil, nutmeg oil, thymol, turmeric oil, etc.), some were fungicidal at higher concentrations (e.g., anethole, catnip oil). Some of the PEs were fungistatic by fumigation and fungicidal by contact action (e.g., cinnamon oil, clove oil, etc). On the other hand, lemon eucalyptous oil was fungicidal by fumigation and by contact at higher concentrations. Surprisingly, castor oil was neither fungistatic nor fungicidal by fumigation or by contact action. Pennyroyal oil was fungistatic at low concentration, but fungicidal at higher concentrations, both by contact and fumigation actions. Allyisothiocynate was fungicidal both by fumigation and contact actions at all concentrations tested.

Soil amendments of selected plant extracts were tested for phytotoxicity as well as suppression of pre-emergence and seedling damping off of cucumber caused by R. solani in the greenhouse (Table 2). We observed that most of the chemicals were not phytotoxic in terms of cucumber seed germination and seedling growth when used as described above. However, both carvacrol and basil oil slightly inhibited cucumber seed germination. In the greenhouse assay (Table 2) we observed that allylisothiocynate, clove oil, geraniol, lemongrass, origanum, pennyroyal, and peppermint oil as soil amendments at 0.3% (v/w) gave >70% suppression of damping off, which compared well with the soil treatment with a popular fungicide Banrot® 40WP. Whereas castor oil was not suppressive to R. solani by contact or fumigative action, it surprisingly gave rise to 83% disease suppression when used as soil amendment (Table 2 and FIG. 1). In general, we found that good in vitro test results corresponded well with disease protection in the soil—plant bioassays. However, exceptions have been reported in the literature where many compounds do exhibit excellent activity in vitro evaluation but fail to demonstrate similar activity in vivo (Letessier, M. P., et al., Journal of Phytopathology, 149: 673-678 (2001)), Feng, W., and X. Zheng, J. Applied Microbiology, 101: 1317-1322 (2006)); the opposite is not common, to have no in vitro activity but profound in vivo activity. Thus castor oil as natural product-GRAS fungicide surprisingly proved to be a rare case.

We have thus surprisingly discovered that castor oil effectively controlled a soilborne fungus Rhizoctonia solani that causes damping off of cucumber seedlings with no noticeable phytotoxicity under greenhouse conditions. In addition, we believe that castor oil, alone or in combination with other GRAS chemicals (e.g., pennyroyal oil) have potential to serve as botanical, sustainable and eco-friendly alternative eradicants as well as protective fungicides to be potentially useful in managing fungal diseases of many economically important plants in greenhouses.

Thus castor oil has potential as a plant-based fungicidal agent to be highly useful alternative to synthetic pesticides to control plant diseases when used as fumigation or soil amendments of potting or field soil.

All of the references cited herein, including U.S. Patents, are incorporated by reference in their entirety. Also incorporated by reference in their entirety are the following references: Ahmed et al., JAOCS 62: 1578-1580 (1985); Bagamboula, C. F., et al., Food Microbiol., 21: 33-42 (2004), DOI: 10.1016/S0740-0020(03)00046-7; Bowers, J. H., and J. C. Locke, Plant Disease, 84: 300-305 (2004); Bowers, J. H., and J. C. Locke, Plant Disease, 88:11-16 (2004); Brent, K. J., 1995, Fungicide resistance in the crop pathogens: How can it be managed? GIFAP, FRAC monograph no. 1; Deans, S. G., and G. Ritchie, International Journal of Food Microbiology, 5:165-180 (1987); Feng, W., and X. Zheng, Journal of Applied Microbiology, 101: 1317-1322 (2006).; Friedman, M., et al., Journal of Food Protection. 65:1545-1560 (2002); Huang, Q., and D. K. Lakshman, Journal of Plant Pathology, 92 (3): 701-707 (2010); Hüsnü, K., et al., (Eds.), Handbook of Essential Oils—Science, Technology, and Applications, 2009, CRC Press, Boca Raton, Fla., pp. 991, ISBN-10: 9781420063158); Lumsden, R. D., et al., Evaluation of Gliocladium virens for biocontrol of Pythium and Rhizoctonia damping-off of bedding plants at four greenhouse locations, 1988-89, Biological and cultural tests, 5: 90 (1990); Letessier M. P. et al., Journal of Phytopathology 149: 673-678 (2001). Meena, M. R., and V. Sethi, Journal of Food Science and Technology, 31:68-70 (1994); Oka, Y., et al., Phytopathology, 90: 710-715 (2000); Novak et al., JAOCS 38:321-324 (1961); Pandey U. K., et al., Z. pflanzenkrank Pflanzenschuz., 89: 344-349 (1982); Pradhanang, P. M., et al., Plant Disease, 87:423-427 (2003); Rhayour, K., et al., Journal of Essential Oil Research, 15:356-362 (2003); Stephens, C. T., and C. C. Powell, Plant Disease, 66: 731-733 (1982); Strider, D. L., and R. K. Jones, 1985, Diseases of Floral Crops, Vol. 2, D. L. Strider, ed., Praeger Publishers. New York; Thompson, D. P., and C. Cannon, Innovative Food Science and Emerging Technologies, 8: 253-258 (1986); Pradhanang, P. M., et al., Plant Disease, 87:423-427 (2003); Sangwan, N. K., et al., Pesticide Science, 28:331-335 (1990); Walker, J. T., and J. B. Melin, Suppl. To the Journal of Nematology, 28(4S):692-635 (1996); U.S. Pat. No. 6,844,353.

Thus, in view of the above, the present invention concerns (in part) the following:

A composition for treating fungal activity in plants or soil, comprising (or consisting essentially of or consisting of) castor oil, water, at least one surface active agent, optionally pennyroyal oil, and optionally an agriculturally acceptable carrier. The above composition, wherein said composition does not contain chitosan salt(s). The above composition, wherein the only oil contained in said composition is castor oil and optionally pennyroyal oil.

A method of treating fungal activity in plants or soil, comprising (or consisting essentially of or consisting of) administering to the plant or soil an effective fungal treating amount of castor oil, water, at least one surface active agent, optionally pennyroyal oil, and optionally an agriculturally acceptable carrier.

The above method, wherein said method does not utilize chitosan salt(s).

The above method, wherein the only oil utilized in said method is castor oil and optionally pennyroyal oil.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Effect of fumigation and contact actions of plant extracts on the in vitro growth of *Rhizoctonia solani*.

|   | amount oil μL/20 mL plate | Fumig1 % inhibition | Fumig2 % inhibition | Effect | PoisonB1 % inhibition | PoisonB2 % inhibition | Effect |
|---|---|---|---|---|---|---|---|
| Allylanisole | 15 | 95 | 97 | S | 94 | 13 | S |
|  | 30 | 97 | 102 | S | 100 | 56 | S |
|  | 45 | 97 | 102 | S | 100 | 92 | S |
|  | 60 | 97 | 100 | S | 100 | 100 | S |
|  | 75 | 98 | 103 | S | 100 | 100 | S |
|  | 150 | 99 | 103 | S | 100 | 100 | S |
| Allylisothiocyanate | 15 | 100 | 100 | C | 100 | 100 | C |
|  | 30 | 100 | 100 | C | 100 | 100 | C |
|  | 45 | 100 | 100 | C | 100 | 100 | C |
|  | 60 | 100 | 100 | C | 100 | 100 | C |
|  | 75 | 100 | 100 | C | 100 | 100 | C |
|  | 150 | 100 | 100 | C | 100 | 100 | C |
| Amyris | 15 | 0 | 90 | S | 79 | 25.00 | S |
|  | 30 | 0 | 85 | S | 88 | 58.00 | S |
|  | 45 | 0 | 89 | S | 90 | 78.00 | S |
|  | 60 | 0 | 89 | S | 88 | 91.00 | S |
|  | 75 | 0 | 97 | S | 90 | 89.00 | S |
|  | 150 | 0 | 102 | S | 94 | 99.00 | S |
| Anethole | 15 | 99 | 90 | S | 100 | 100 | S |
|  | 30 | 100 | 85 | S | 100 | 100 | S |
|  | 45 | 100 | 86 | S | 100 | 100 | C |
|  | 60 | 100 | 89 | S | 100 | 100 | C |
|  | 75 | 100 | 97 | S | 100 | 100 | C |
|  | 150 | 100 | 102 | S | 100 | 100 | C |
| Anise | 15 | 97 | 94 | S | 100 | 100 | S |
|  | 30 | 98 | 92 | S | 100 | 100 | S |
|  | 45 | 98 | 96 | S | 100 | 100 | C |
|  | 60 | 97 | 99 | S | 100 | 100 | C |
|  | 75 | 95 | 100 | S | 100 | 100 | C |
|  | 150 | 100 | 97 | S | 100 | 100 | C |
| Banrot | 15 |  |  |  | 100 | 100 | S |
|  | 30 |  |  |  | 100 | 100 | S |
|  | 45 |  |  |  | 100 | 100 | S |
|  | 60 |  |  |  | 100 | 100 | S |
|  | 75 |  |  |  | 100 | 100 | S |
|  | 150 |  |  |  | 100 | 100 | S |
| Basil | 15 | 93 | 88 | S | 34 | 32.22 | S |
|  | 30 | 95 | 88 | S | 85 | 72.50 | S |
|  | 45 | 99 | 87 | S | 100 | 100.00 | S |
|  | 60 | 97 | 91 | S | 100 | 100.00 | S |
|  | 75 | 96 | 90 | S | 100 | 100.00 | C |
|  | 150 | 97 | 89 | S | 100 | 100.00 | C |
| Bay | 15 | 86 | 68 | S | 100 | 100 | C |
|  | 30 | 88 | 75 | S | 100 | 100 | C |
|  | 45 | 98 | 82 | S | 100 | 100 | C |
|  | 60 | 93 | 85 | S | 100 | 100 | C |
|  | 75 | 94 | 88 | S | 100 | 100 | C |
|  | 150 | 93 | 97 | S | 100 | 100 | C |
| Carvacrol | 15 | 88 | 87 | S | 100 | 100 | C |
|  | 30 | 94 | 91 | S | 100 | 100 | C |
|  | 45 | 100 | 91 | S | 100 | 100 | C |
|  | 60 | 100 | 93 | S | 100 | 100 | C |
|  | 75 | 99 | 96 | S | 100 | 100 | C |
|  | 150 | 100 | 100 | S | 100 | 100 | C |

TABLE 1-continued

Effect of fumigation and contact actions of plant extracts on the in vitro growth of *Rhizoctonia solani*.

| | amount oil μL/20 mL plate | Fumig1 % inhibition | Fumig2 % inhibition | Effect | PoisonB1 % inhibition | PoisonB2 % inhibition | Effect |
|---|---|---|---|---|---|---|---|
| Castor | 15 | 0 | 0 | n/a | 0 | 0 | S |
| | 30 | 0 | 0 | n/a | 0 | 0 | S |
| | 45 | 0 | 0 | n/a | 0 | 0 | S |
| | 60 | 0 | 0 | n/a | 0 | 0 | S |
| | 75 | 0 | 0 | n/a | 0 | 0 | S |
| | 150 | 0 | 0 | n/a | 0 | 0 | S |
| Catnip | 15 | 51 | 50 | S | 100 | 98 | S |
| | 30 | 58 | 67 | S | 100 | 100 | C |
| | 45 | 68 | 63 | S | 100 | 100 | C |
| | 60 | 71 | 65 | S | 100 | 100 | C |
| | 75 | 70 | 65 | S | 100 | 100 | C |
| | 150 | 73 | 78 | S | 100 | 100 | C |
| Cedar | 15 | 46 | 46 | S | 53 | 17 | S |
| | 30 | 44 | 48 | S | 60 | 47 | S |
| | 45 | 67 | 46 | S | 62 | 52 | S |
| | 60 | 48 | 48 | S | 70 | 45 | S |
| | 75 | 50 | 49 | S | 76 | 68 | S |
| | 150 | 51 | 54 | S | 81 | 60 | S |
| Cinnamon | 15 | 73 | 62 | S | 100 | 100 | C |
| | 30 | 80 | 66 | S | 100 | 100 | C |
| | 45 | 85 | 69 | S | 100 | 100 | C |
| | 60 | 86 | 77 | S | 100 | 100 | C |
| | 75 | 92 | 76 | S | 100 | 100 | C |
| | 150 | 94 | 84 | S | 100 | 100 | C |
| Clove | 15 | 70 | 51 | S | 100 | 100 | C |
| | 30 | 75 | 54 | S | 100 | 100 | C |
| | 45 | 84 | 63 | S | 100 | 100 | C |
| | 60 | 88 | 68 | S | 100 | 100 | C |
| | 75 | 89 | 67 | S | 100 | 100 | C |
| | 150 | 90 | 76 | S | 100 | 100 | C |
| coconut | 15 | 0 | | n/a | 41 | 100 | C |
| | 30 | 0 | | n/a | 40 | 100 | S |
| | 45 | 0 | | n/a | 39 | 100 | S |
| | 60 | 0 | | n/a | 39 | 100 | S |
| | 75 | 0 | | n/a | 46 | 100 | S |
| | 150 | 0 | | n/a | 41 | 100 | S |
| Geraniol | 15 | 51 | 15 | S | 100 | 100 | C |
| | 30 | 56 | 34 | S | 100 | 100 | C |
| | 45 | 62 | 31 | S | 100 | 100 | C |
| | 60 | 66 | 54 | S | 100 | 100 | C |
| | 75 | 73 | 67 | S | 100 | 100 | C |
| | 150 | 77 | 61 | S | 100 | 100 | C |
| Karanj seed | 15 | 0 | 0 | n/a | 56 | 38 | S |
| | 30 | 0 | 0 | n/a | 51 | 36 | S |
| | 45 | 0 | 0 | n/a | 31 | 41 | S |
| | 60 | 0 | 0 | n/a | 37 | 44 | S |
| | 75 | 0 | 0 | n/a | 46 | 48 | S |
| | 150 | 0 | 0 | n/a | 43 | 49 | S |
| Lemon eucalyptus | 15 | 100 | 100 | C | 69 | 88 | S |
| | 30 | 100 | 100 | C | 100 | 100 | S |
| | 45 | 100 | 100 | C | 100 | 100 | C |
| | 60 | 100 | 100 | C | 100 | 100 | C |
| | 75 | 100 | 100 | C | 100 | 100 | C |
| | 150 | 100 | 100 | C | 100 | 100 | C |
| Lemongrass | 15 | 97 | 84 | S | 100 | 100 | C |
| | 30 | 100 | 91 | S | 100 | 100 | C |
| | 45 | 99 | 100 | S | 100 | 100 | C |
| | 60 | 100 | 99 | S | 100 | 100 | C |
| | 75 | 100 | 100 | S | 100 | 100 | C |
| | 150 | 100 | 100 | C | 100 | 100 | C |
| Myrrh | 15 | 44 | 62 | S | 79 | 43 | S |
| | 30 | 44 | 42 | S | 81 | 54 | S |
| | 45 | 45 | 63 | S | 83 | 59 | S |
| | 60 | 53 | 47 | S | 83 | 63 | S |
| | 75 | 52 | 56 | S | 85 | 76 | S |
| | 150 | 49 | 70 | S | 88 | 79 | S |
| Nerolidol | 15 | 0 | 0 | S | 71 | 78 | S |
| | 30 | 0 | 40 | S | 78 | 81 | S |
| | 45 | 0 | 42 | S | 83 | 87 | S |
| | 60 | 0 | 41 | S | 84 | 90 | S |
| | 75 | 0 | 42 | S | 87 | 92 | S |
| | 150 | 0 | 41 | S | 89 | 99 | S |

TABLE 1-continued

Effect of fumigation and contact actions of plant extracts on the in vitro growth of *Rhizoctonia solani*.

| | amount oil µL/20 mL plate | Fumig1 % inhibition | Fumig2 % inhibition | Effect | PoisonB1 % inhibition | PoisonB2 % inhibition | Effect |
|---|---|---|---|---|---|---|---|
| Nutmeg | 15 | 61 | 78 | S | 84 | 42.22 | S |
| | 30 | 76 | 84 | S | 94 | 76.94 | S |
| | 45 | 84 | 92 | S | 100 | 86.11 | S |
| | 60 | 87 | 86 | S | 100 | 94.17 | S |
| | 75 | 89 | 96 | S | 100 | 100 | S |
| | 150 | 90 | 100 | S | 100 | 100 | S |
| Orange | 15 | 0 | 0 | S | 6 | 0 | C |
| | 30 | 0 | 0 | S | 22 | 0 | C |
| | 45 | 0 | 45 | S | 26 | 0 | C |
| | 60 | 0 | 58 | S | 34 | 0 | C |
| | 75 | 0 | 60 | S | 38 | 0 | C |
| | 150 | 45 | 86 | S | 74 | 0 | C |
| Origanum | 15 | 100 | 92 | S | 100 | 100 | S |
| | 30 | 99 | 92 | S | 100 | 100 | C |
| | 45 | 99 | 95 | S | 100 | 100 | C |
| | 60 | 98 | 92 | S | 100 | 100 | C |
| | 75 | 98 | 95 | C | 100 | 100 | C |
| | 150 | 98 | 98 | C | 100 | 100 | C |
| Palmerosa | 15 | 39 | 39 | S | 63.06 | 76 | S |
| | 30 | 40 | 42 | S | 100 | 100 | C |
| | 45 | 48 | 50 | S | 100 | 100 | C |
| | 60 | 53 | 54 | S | 100 | 100 | C |
| | 75 | 54 | 57 | S | 100 | 100 | C |
| | 150 | 69 | 72 | S | 100 | 100 | C |
| Pennyroyal | 15 | 96 | 97 | S | 100 | 100 | S |
| | 30 | 100 | 96 | C | 100 | 100 | C |
| | 45 | 98 | 96 | C | 100 | 100 | C |
| | 60 | 100 | 96 | C | 100 | 100 | C |
| | 75 | 100 | 96 | C | 100 | 100 | C |
| | 150 | 100 | 95 | C | 100 | 100 | C |
| Peppermint | 15 | 100 | 100 | S | 52 | 86.39 | C |
| | 30 | 100 | 100 | S | 100 | 100.00 | C |
| | 45 | 100 | 100 | S | 100 | 100.00 | C |
| | 60 | 100 | 100 | S | 100 | 100.00 | C |
| | 75 | 100 | 100 | S | 100 | 100.00 | C |
| | 150 | 100 | 100 | S | 100 | 100.00 | C |
| Pimenta | 15 | 74 | 53 | S | 100 | 100 | S |
| | 30 | 80 | 56 | S | 100 | 100 | S |
| | 45 | 82 | 57 | S | 100 | 100 | S |
| | 60 | 84 | 70 | S | 100 | 100 | S |
| | 75 | 87 | 72 | S | 100 | 100 | S |
| | 150 | 93 | 77 | S | 100 | 100 | S |
| Pink Pepper | 15 | 0 | 0 | n/a | 0.00 | 0.00 | S |
| | 30 | 0 | 0 | n/a | 0.00 | 0.00 | S |
| | 45 | 0 | 0 | n/a | 19.72 | 22.78 | S |
| | 60 | 0 | 0 | n/a | 27.78 | 28.89 | S |
| | 75 | 0 | 0 | n/a | 31.67 | 32.50 | C |
| | 150 | 69 | 67 | S | 30.83 | 51.11 | C |
| Rosemary | 15 | 77 | 54 | S | 47 | 26.67 | S |
| | 30 | 86 | 75 | S | 80 | 79.44 | C |
| | 45 | 98 | 77 | S | 98 | 100.00 | C |
| | 60 | 100 | 97 | S | 100 | 100.00 | C |
| | 75 | 100 | 96 | S | 100 | 100.00 | C |
| | 150 | 100 | 100 | S | 100 | 100.00 | C |
| Spearmint | 15 | 89 | 67 | S | 100 | 100 | S |
| | 30 | 96 | 93 | C | 100 | 100 | S |
| | 45 | 94 | 90 | C | 100 | 100 | S |
| | 60 | 95 | 87 | C | 100 | 100 | S |
| | 75 | 98 | 92 | C | 100 | 100 | S |
| | 150 | 100 | 92 | C | 100 | 100 | S |
| Tangerine | 15 | 0 | 0 | n/a | 0 | 0.00 | S |
| | 30 | 0 | 0 | n/a | 0 | 8.33 | S |
| | 45 | 0 | 0 | n/a | 8.06 | 11.94 | S |
| | 60 | 0 | 0 | n/a | 23.33 | 12.22 | C |
| | 75 | 47 | 47 | n/a | 28.33 | 19.44 | C |
| | 150 | 86 | 71 | n/a | 55 | 34.44 | C |
| Tea Tree | 15 | 39 | 71 | S | 76 | 13.61 | C |
| | 30 | 86 | 97 | S | 100 | 71.67 | C |
| | 45 | 97 | 97 | C | 100 | 99.72 | C |
| | 60 | 100 | 98 | C | 100 | 100.00 | C |
| | 75 | 100 | 100 | C | 100 | 100.00 | C |
| | 150 | 100 | 100 | C | 100 | 100.00 | C |

TABLE 1-continued

Effect of fumigation and contact actions of plant extracts on the in vitro growth of *Rhizoctonia solani*.

| | amount oil μL/20 mL plate | Fumig1 % inhibition | Fumig2 % inhibition | Effect | PoisonB1 % inhibition | PoisonB2 % inhibition | Effect |
|---|---|---|---|---|---|---|---|
| Thymol | 15 | 77 | 91 | S | 100 | 42 | S |
| | 30 | 86 | 93 | S | 100 | 100 | S |
| | 45 | 90 | 94 | S | 100 | 100 | S |
| | 60 | 89 | 100 | S | 100 | 100 | S |
| | 75 | 93 | 100 | S | 100 | 100 | S |
| | 150 | 96 | 100 | S | 100 | 100 | S |
| Turmeric | 15 | 0 | 0 | S | 40 | 0.00 | S |
| | 30 | 0 | 0 | S | 62 | 13.06 | S |
| | 45 | 55 | 0 | S | 82 | 12.50 | S |
| | 60 | 68 | 0 | S | 83 | 24.44 | S |
| | 75 | 89 | 0 | S | 93 | 44.72 | S |
| | 150 | 100 | 0 | S | 100 | 71.94 | S |
| Vetiver | 15 | 0 | 4 | S | 59 | 44 | S |
| | 30 | 0 | 17 | S | 73 | 55 | S |
| | 45 | 0 | 26 | S | 79 | 100 | C |
| | 60 | 0 | 28 | S | 81 | 66 | C |
| | 75 | 0 | 35 | S | 84 | 74 | C |
| | 150 | 47 | 36 | S | 85 | 79 | C |

Two sets of fumigation (Fumig1 and Fumig2) and poison bed (PoisonB1 and PoisonB2) experiments were carried out as described in Materials and Methods.
Possible effect (*) of the plant extracts have been denoted as S = fungistatic, C = fungicidal.

TABLE 2

Effect of soil fumigation and contact actions of selected plant extracts (PE) on suppression of damping off of cucumber seedlings by *Rhizoctonia solani* under greenhouse conditions.

| Treatments | Avg. seed germination (+ PE only) | % Seed germination (+ PE only) | Avg. seed Germination (+ PE + R. solani) | % Disease suppression (+ PE + R. solani) |
|---|---|---|---|---|
| Expt 1. | | | | |
| Soybean oil | 9.67 | 80.60 | 0.00 | 00.00 |
| Bay Oil | 10.67 | 88.91 | 3.00 | 25.00 |
| Carvacrol | 4.00 | 33.33 | 5.67 | 47.25 |
| Cinnamon oil | 10.00 | 83.33 | 1.67 | 13.91 |
| Geraniol | 11.33 | 94.41 | 9.33 | 77.75 |
| Eugenol | 10.00 | 83.33 | 5.33 | 44.42 |
| Lemongrass oil | 8.00 | 66.67 | 12.00 | 100.00 |
| Origanum oil | 10.33 | 86.10 | 9.67 | 80.58 |
| Pennyroyal oil | 8.67 | 72.25 | 9.00 | 75.00 |
| Peppermint oil | 10.33 | 86.10 | 9.00 | 75.00 |
| Rosemary | 9.33 | 77.75 | 6.33 | 52.75 |
| Banrot | | | 10.33 | 86.10 |
| Expt 2. | | | | |
| Soybean oil | 10.33 | 86.10 | 0.00 | 00.00 |
| Allylanisol | 9.00 | 75.00 | 7.00 | 58.33 |
| Allyisothiocynate | 10.33 | 86.10 | 10.67 | 88.92 |
| Anethole | 9.00 | 75.00 | 7.00 | 58.33 |
| Anise oil | 8.33 | 69.42 | 7.67 | 63.92 |
| Basil oil | 5.67 | 47.25 | 5.00 | 41.67 |
| Castor oil | 9.33 | 77.75 | 10.00 | 83.33 |
| Clove oil | 11.67 | 97.25 | 8.67 | 97.25 |
| Pimenta oil | 10.33 | 86.10 | 8.33 | 69.42 |
| Tea tree oil | 12.00 | 100.00 | 7.33 | 61.10 |
| Thymol | 8.00 | 66.67 | 3.33 | 27.75 |
| Banrot | | | 6.7 | 55.83 |
| Expt. 3. | | | | |
| Castor oil | 11 | 100 | 9.33 | 84.81 |

We claim:

1. A method of treating *Rhizoctonia solani* fungal activity in plants or soil in need thereof comprising:
   administering an effective amount of a composition comprising castor oil, pennyroyal oil, water, at least one surface active agent, and an agriculturally acceptable carrier to said plants and/or soil,
   wherein the administered composition exhibits fungicidal or fungistatic activity against the *Rhizoctonia solani*.

2. A method of treating *Rhizoctonia solani* fungal activity in plants or soil in need thereof comprising:
   administering an effective amount of a composition comprising castor oil, water, at least one surface active agent, and an agriculturally acceptable carrier to said soil,
   wherein the administered composition exhibits fungicidal or fungistatic activity against the *Rhizoctonia solani*.

* * * * *